(12) United States Patent
Lobo et al.

(10) Patent No.: US 11,564,708 B2
(45) Date of Patent: Jan. 31, 2023

(54) CANNULA ASSEMBLY INCLUDING AN ADJUSTABLE ELONGATE SHAFT ASSEMBLY

(71) Applicant: Covidien LP, Mansfield, MA (US)

(72) Inventors: Astley C. Lobo, West Haven, CT (US); Kevin Desjardin, Prospect, CT (US); Douglas M. Pattison, East Hartford, CT (US); Christopher A. Tokarz, Torrington, CT (US); Oksana Buyda, East Haven, CT (US); Amanda M. Adinolfi, Wallingford, CT (US)

( * ) Notice: Subject to any disclaimer, the term of this patent is extended or adjusted under 35 U.S.C. 154(b) by 326 days.

(21) Appl. No.: 16/901,657

(22) Filed: Jun. 15, 2020

(65) Prior Publication Data

US 2021/0386454 A1 Dec. 16, 2021

(51) Int. Cl.
- A61B 17/34 (2006.01)
- A61B 17/00 (2006.01)
- A61M 25/01 (2006.01)

(52) U.S. Cl.
CPC .... *A61B 17/3421* (2013.01); *A61B 17/00234* (2013.01); *A61B 2017/00991* (2013.01); *A61B 2017/3419* (2013.01); *A61B 2017/3425* (2013.01); *A61B 2017/3443* (2013.01); *A61B 2017/3449* (2013.01); *A61M 2025/0175* (2013.01)

(58) Field of Classification Search
CPC .......... A61B 17/3421; A61B 17/3423; A61B 17/3431; A61B 17/3439; A61B 17/3403; A61B 17/00234; A61B 2017/00991; A61B 2017/3443; A61B 2017/3425; A61B 2017/3419; A61B 2017/3449; A61M 2025/0175

USPC ............. 600/104, 204, 205, 206, 208, 215
See application file for complete search history.

(56) References Cited

U.S. PATENT DOCUMENTS

| | | | |
|---|---|---|---|
| 397,060 | A | 1/1889 | Knapp |
| 512,456 | A | 1/1894 | Sadikova |
| 1,213,005 | A | 1/1917 | Pillsbury |
| 2,912,981 | A | 11/1959 | Keough |
| 2,936,760 | A | 5/1960 | Gains |
| 3,039,468 | A | 6/1962 | Price |
| 3,050,066 | A | 8/1962 | Koehn |
| 3,253,594 | A | 5/1966 | Matthews et al. |

(Continued)

FOREIGN PATENT DOCUMENTS

| | | |
|---|---|---|
| EP | 0480653 A1 | 4/1992 |
| EP | 0610099 A2 | 8/1994 |

(Continued)

OTHER PUBLICATIONS

Extended European Search Report issued in corresponding European Application No. 21175052.6 dated Nov. 5, 2021, 12 pages.

*Primary Examiner* — Marcela I. Shirsat
(74) *Attorney, Agent, or Firm* — Carter, DeLuca & Farrell LLP (57) ABSTRACT

A cannula assembly includes an elongate shaft assembly that is adjustable by a clinician to vary the length of the cannula assembly. In particular, the elongate shaft assembly may be transitioned to provide various lengths of the cannula assembly by selectively positioning a plurality of segments of the elongate shaft assembly. In this manner, a single cannula assembly may be tailored to each patient or a surgical procedure being performed.

20 Claims, 9 Drawing Sheets

(56) References Cited

U.S. PATENT DOCUMENTS

| | | |
|---|---|---|
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 8,454,645 B2 | 6/2013 | Criscuolo et al. |
| 2003/0236505 A1 | 12/2003 | Bonadio et al. |
| 2004/0260246 A1* | 12/2004 | Desmond ........... A61B 17/3421 |
| | | 604/174 |

(56) References Cited

U.S. PATENT DOCUMENTS

| | | | |
|---|---|---|---|
| 2006/0200185 A1* | 9/2006 | Marchek ............ | A61B 17/3421 |
| | | | 606/191 |
| 2006/0200186 A1* | 9/2006 | Marchek ............ | A61B 17/0218 |
| | | | 606/191 |
| 2010/0268241 A1 | 10/2010 | Flom et al. | |
| 2019/0307937 A1 | 10/2019 | Fitzgerald et al. | |

FOREIGN PATENT DOCUMENTS

| | | | |
|---|---|---|---|
| EP | 0880939 A1 | 12/1998 | |
| WO | 9206638 A1 | 4/1992 | |
| WO | 9218056 A1 | 10/1992 | |
| WO | 9221293 A1 | 12/1992 | |
| WO | 9221295 A1 | 12/1992 | |
| WO | 9309722 A1 | 5/1993 | |
| WO | 9721461 A1 | 6/1997 | |
| WO | 9912602 A1 | 3/1999 | |
| WO | 0126724 A2 | 4/2001 | |
| WO | 02096307 A2 | 12/2002 | |
| WO | 2004032756 A2 | 4/2004 | |
| WO | WO-2018094458 A1 * | 5/2018 | ......... A61B 17/3403 |
| WO | 2018165367 A1 | 9/2018 | |

* cited by examiner

CANNULA ASSEMBLY INCLUDING AN ADJUSTABLE ELONGATE SHAFT ASSEMBLY

FIELD

The disclosure relates generally to surgical instruments, and more particularly, to a cannula assembly having an adjustable elongate shaft assembly.

BACKGROUND

Minimally invasive surgical procedures, including endoscopic, laparoscopic and arthroscopic procedures, have been used for introducing surgical instruments inside a patient and for viewing portions of the patient's anatomy. Forming a relatively small diameter, temporary pathway to the surgical site is a key feature of most minimally invasive surgical procedures. The most common method of providing such a pathway is by inserting a cannula assembly through the skin.

Obturators are typically designed with a tip that may be used to form an opening through the abdominal wall. An obturator is inserted into a cannula, and then the combined obturator and cannula are together placed against the skin to be penetrated. In order to penetrate the skin, the distal end of the obturator engages the skin, which may or may not have been previously cut with a scalpel. The obturator is then used to penetrate the skin and access the body cavity. By applying pressure against the proximal end of the obturator, the tip of the obturator is forced though the skin and the underlying tissue layers until the cannula and obturator enter the body cavity. The obturator is then withdrawn. The cannula remains in place through the incision for use during the minimally invasive procedure.

SUMMARY

In accordance with the disclosure, a cannula assembly includes a cannula housing and an elongate shaft assembly extending from the cannula housing. The elongate shaft assembly defines a lumen in communication with the cannula housing. The elongate shaft assembly includes a first segment coupled to the cannula housing, a second segment slidable relative to the first segment, and a third segment slidable relative to the second segment. The elongate shaft assembly is transitionable to a retracted configuration, in which, the cannula assembly has a first length, an intermediate configuration, in which, the cannula assembly has a second length greater than the first length, and an extended configuration, in which, the cannula assembly has a third length greater than the second length.

In an aspect, the first segment may include a first circular protrusion extending radially inward from an inner surface of the first segment.

In another aspect, the first circular protrusion may be disposed in a distal end portion of the first segment.

In yet another aspect, the second segment may include a proximal circular groove configured to receive the first circular protrusion of the first segment.

In an aspect, the second segment may include a distal circular groove configured to receive the first circular protrusion of the first segment.

In another aspect, the second segment may include a second circular protrusion extending radially inward from an inner surface of the second segment.

In yet another aspect, the second circular protrusion of the second segment may be disposed adjacent a distal end portion of the second segment.

In still yet another aspect, the third segment may include proximal and distal circular grooves configured to receive the second circular protrusion of the second segment.

In still yet another aspect, the second segment may include a gasket engaging an inner surface of the first segment in a sealing relation.

In an aspect, the gasket may be disposed in a proximal portion of the second segment.

In another aspect, the second segment may include an engaging portion defining a circular recess supporting the gasket mounted thereabout.

In yet another aspect, the engaging portion may be radially deflectable.

In still yet another aspect, the cannula housing may include a base portion coupled to the first segment extending therefrom and a seal assembly detachably coupled to the base portion.

In accordance with another aspect of the disclosure, a cannula assembly includes a cannula housing configured to receive a surgical instrument therethrough, and an elongate shaft assembly coupled to the cannula housing. The elongate shaft assembly is adjustable to selectively vary a length of the cannula assembly. The elongate shaft assembly defines a lumen configured to receive the surgical instrument inserted through the cannula housing. The elongate shaft assembly includes a first segment coupled to the housing, a second segment slidably extending from the first segment, and a third segment slidably extending from the second segment. The elongate shaft assembly is transitionable to a retracted configuration, an intermediate configuration, and an extended configuration. In the retracted configuration, a proximal portion of the second segment is disposed adjacent a proximal portion of the first segment and a proximal portion of the third segment is disposed adjacent the proximal portion of the second segment. In the intermediate configuration, the proximal portion of the second segment is disposed adjacent a distal portion of the first segment and the proximal portion of the third segment is adjacent the proximal portion of the second segment. In the extended configuration, the proximal portion of the second segment is disposed adjacent the distal portion of the first segment and the proximal portion of the third segment is disposed adjacent a distal portion of the second segment.

In an aspect, the first, second, and third segments may be concentrically arranged.

In another aspect, the second segment may engage an inner surface of the first segment in a sealing relation.

In yet another aspect, the third segment may engage an inner surface of the second segment in a sealing relation.

In still yet another aspect, the first segment may include a mating portion at the distal portion thereof.

In an aspect, the second segment may include proximal and distal mating portions complementary to the first mating portion of the first segment to inhibit axial displacement of the second segment relative to the first segment.

In another aspect, the second segment may include a mating part, and the third segment may include proximal and distal mating parts complementary to the mating part of the second segment to inhibit axial displacement of the third segment relative to the second segment.

BRIEF DESCRIPTION OF DRAWINGS

A cannula assembly is disclosed herein with reference to the drawings, wherein.

DETAILED DESCRIPTION

A cannula assembly is described in detail with reference to the drawings, wherein like reference numerals designate corresponding elements in each of the several views. As used herein, the term "distal" refers to that portion of the instrument, or component thereof which is farther from the user while the term "proximal" refers to that portion of the instrument or component thereof which is closer to the user. In addition, the terms parallel and perpendicular are understood to include relative configurations that are substantially parallel and substantially perpendicular up to about + or –10 degrees from true parallel and true perpendicular. Further, to the extent consistent, any or all of the aspects detailed herein may be used in conjunction with any or all of the other aspects detailed herein.

Figure 1:
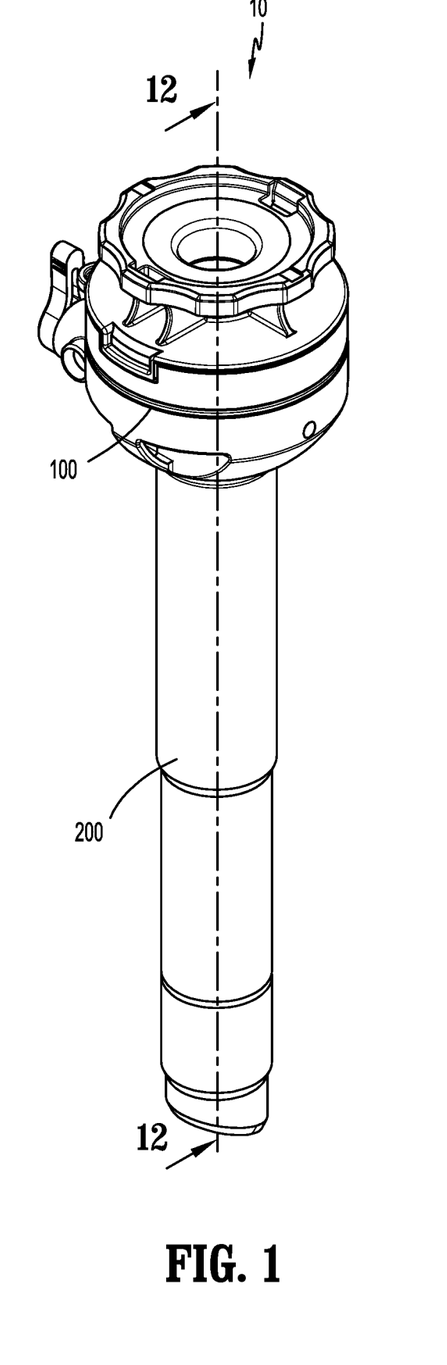
FIG. 1 is a perspective view of a cannula assembly in accordance with the disclosure.
Figure 2:
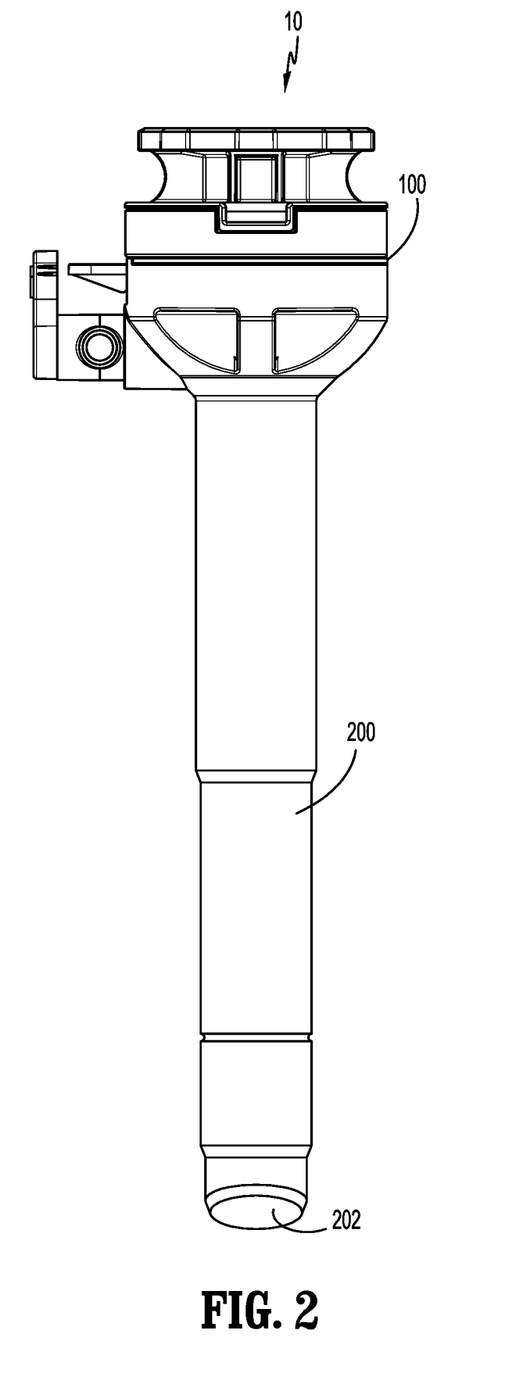
FIG. 2 is a side view of the cannula assembly of FIG. 1.

FIGS. 1 and 2 illustrate a cannula assembly in accordance with the disclosure shown generally as 10. The cannula assembly 10 is configured to permit access to a surgical site such as, e.g., an insufflated abdominal cavity, during a laparoscopic procedure to permit the introduction of a surgical object for performing various surgical tasks on internal organs within the cavity. The surgical object may be a surgical instrument such as laparoscopic or endoscopic clip appliers, obturators, graspers, dissectors, retractors, staplers, laser probes, photographic devices, tubes, endoscopes and laparoscopes, electro-surgical devices and the like. The cannula assembly 10 generally includes a cannula housing 100 and an elongate shaft assembly 200 extending from the cannula housing 100. The elongate shaft assembly 200 is adjustable by a clinician to vary the length of the elongate shaft assembly 200. In this manner, a single cannula assembly 10 may be tailored to a particular patient or a surgical procedure. For example, the elongate shaft assembly 200 may be adjusted for different tissue thicknesses, as will be discussed below.

Figure 3:
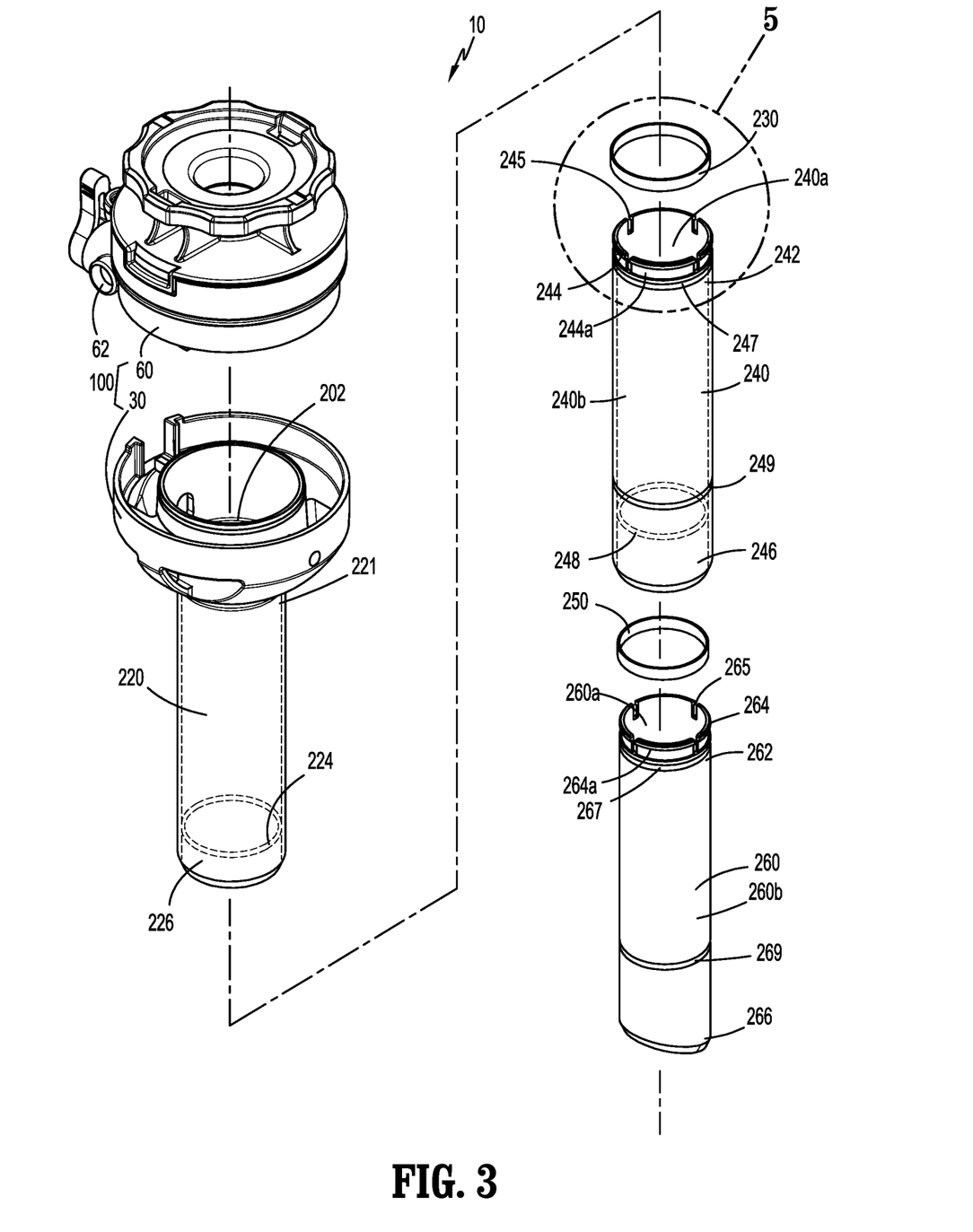
FIG. 3 is an exploded perspective view of the cannula assembly of FIG. 1 with parts separated.

FIGS. 2 and 3 illustrate the cannula housing 100 configured for engagement by the clinician. The cannula housing 100 includes a base portion 30 and a seal assembly 60 detachably coupled to the base portion 30. The base portion 30 is coupled to the elongate shaft assembly 200 including first, second, and third segments 220, 240, 260. The seal assembly 60 includes one or more internal seals adapted to establish a seal about a surgical object "I" (FIG. 9) introduced therethrough. The cannula housing 100 also includes an insufflation connector 62 (e.g., a luer connector) for connecting to a source of insufflation fluids for delivery within, e.g., the abdominal cavity. A longitudinal lumen 202 (FIG. 2) defined by the elongate shaft assembly 200 is in fluid communication with the insufflation connector 62 to convey the insufflation fluids into the abdominal cavity to establish and/or maintain the pneumoperitoneum.

Figure 4:
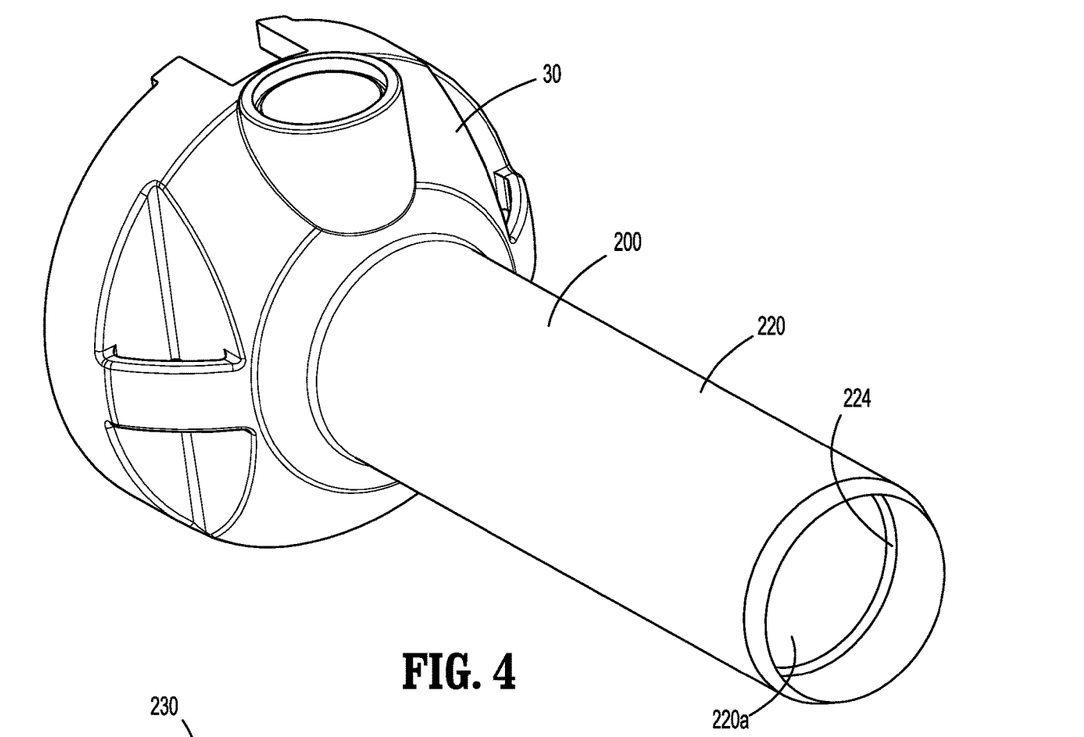
FIG. 4 is a partial perspective view of the cannula assembly of FIG. 1.

FIGS. 2-4 illustrate the elongate shaft assembly 200 including the first, second, and third segments 220, 240, 260 that are slidably nested (e.g., a telescopic arrangement) to enable the clinician to selectively adjust the length of the elongate shaft assembly 200. The first segment 220 is coupled to the base portion 30 of the cannula housing 100 by, e.g., welding or gluing. Alternatively, the first segment 220 may be integrally formed with the base portion 30. The first, second, and third segments 220, 240, 260 may be concentrically arranged. In particular, the second segment 240 is slidably received in a first lumen 220a of the first segment 220, and the third segment 260 is slidably received in a second lumen 240a of the second segment 240. It is contemplated that the number of segments could be two, three or more with various lengths of the segments.

Figure 5:
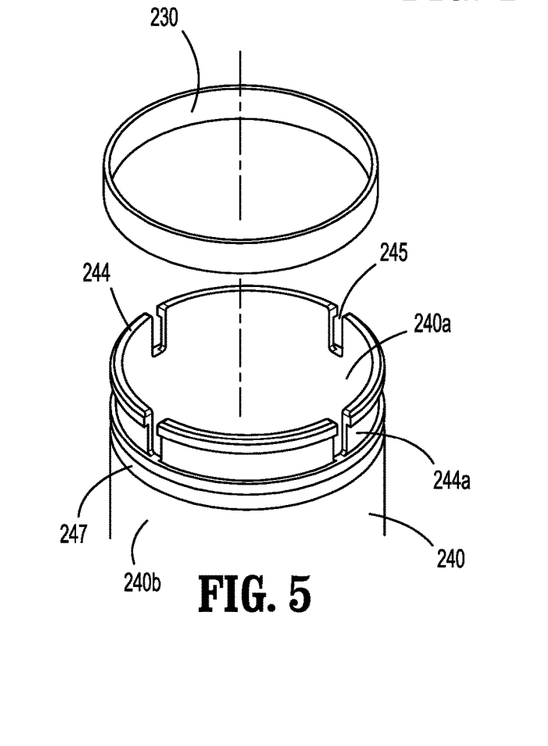
FIG. 5 is an enlarged perspective view of the indicated area of detail of FIG. 3.
Figure 6:
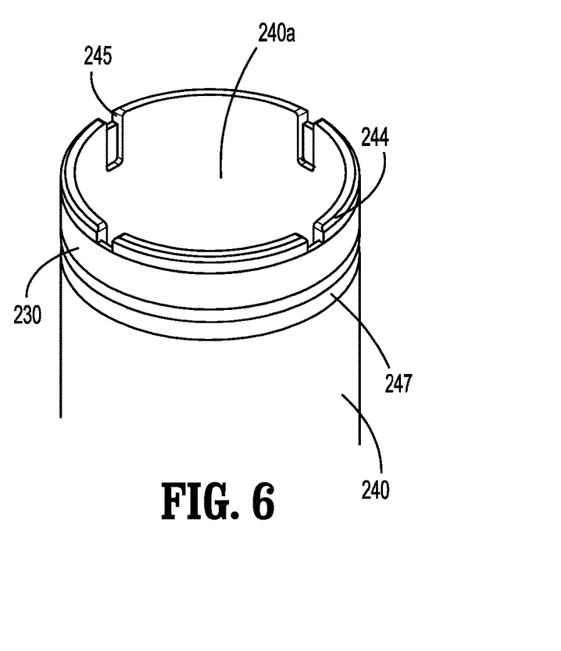
FIG. 6 is a partial perspective view of the second segment of FIG. 5, illustrating a gasket mounted on a second segment of an elongate shaft assembly.

The first segment 220 includes a proximal end portion 221 coupled to the base portion 30, and a distal end portion 226 having a first circular protrusion 224. The first circular protrusion 224 extends radially inward from an inner surface of the first segment 220. The second segment 240 includes a proximal end portion 242 and a distal end portion 246. FIGS. 5 and 6 illustrate the proximal end portion 242 including an engaging portion 244 defining a circular recess 244a configured to support a gasket 230 therein such that the gasket 230 engages the inner wall of the first segment 220 and provides a hermetic seal against the inner wall. In particular, the engaging portion 244 further defines a plurality of slots 245 circumferentially arranged about the second lumen 240a. Each slot 245 extends along a length of the second segment 240. The plurality of slots 245 enables the partitioned portions of the engaging portion 244 to deflect radially to facilitate slidable displacement of the second segment 240 relative to the first segment 220. The distal end portion 246 defines a distal circular groove 249 defined in an outer surface 240b of the second segment 240. The distal end portion 246 includes a second circular protrusion 248 extending radially inward from an inner surface of the second segment 240. In an aspect, the second circular protrusion 248 may be distal of the distal circular groove 249.

With continued reference to FIG. 3, the third segment 260 of the elongate shaft assembly 200 includes a proximal end portion 262 and a distal end portion 266. The proximal end portion 262 includes an engaging portion 264 defining a circular recess 264a supporting a gasket 250 therein such that the gasket 250 engages the inner wall of the second segment 240 and provides a hermetic seal against the inner wall. In particular, the engaging portion 264 further defines a plurality of slots 265 circumferentially arranged about a third lumen 260a defined through the third segment 260. Each slot 265 extends along a length of the third segment 260. The plurality of slots 265 enables the partitioned portions of the engaging portion 264 to deflect radially to facilitate slidable displacement of the third segment 260 relative to the second segment 240. The third segment 260 further defines a proximal circular groove 267 in an outer surface 260b of the third segment 260 and adjacent the engaging portion 264. For example, the proximal circular groove 267 may be distal of the engaging portion 264. The third segment 260 further defines a distal circular groove 269 defined in the outer surface 260b of the third segment 260. The distal circular groove 269 may be adjacent the distal end portion 266.

The elongate shaft assembly 200 is adjustable to provide variable lengths of the cannula assembly 10. In particular, the elongate shaft assembly 200 may be adjustable to provide a first length of the cannula assembly 10, in which, the elongate shaft assembly 200 is in a retracted configuration, a second length of the cannula assembly 10, in which, the elongate shaft assembly 200 is in an intermediate configuration, and a third length of the cannula assembly 10, in which, the elongate shaft 200 is in an extended configuration. In the retracted state, the exposed surfaces of the first and second segments 220, 240 may have fixation ribs to retain the cannula within tissue when instruments or obturator is retracted through the longitudinal lumen 202 and the seal assembly 60.

Figure 7:
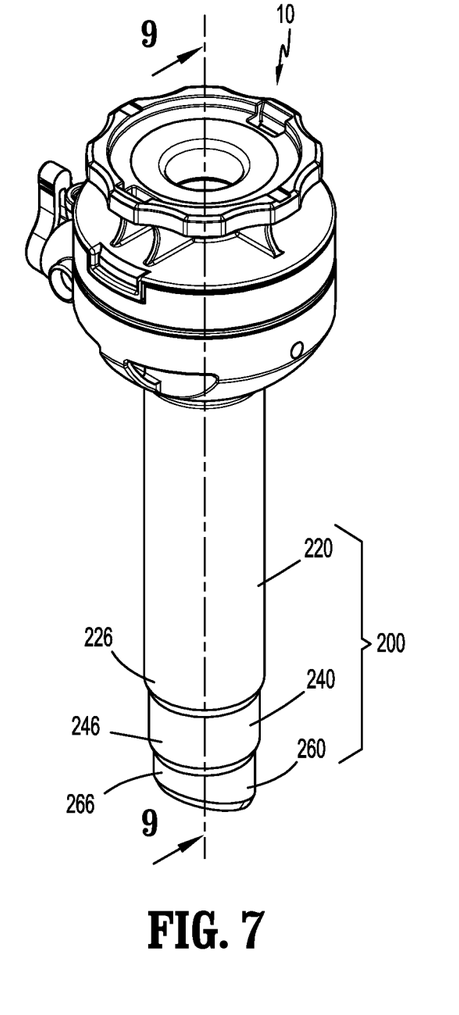
FIG. 7 is a perspective view of the cannula assembly of FIG. 1 in a retracted configuration.
Figure 8:
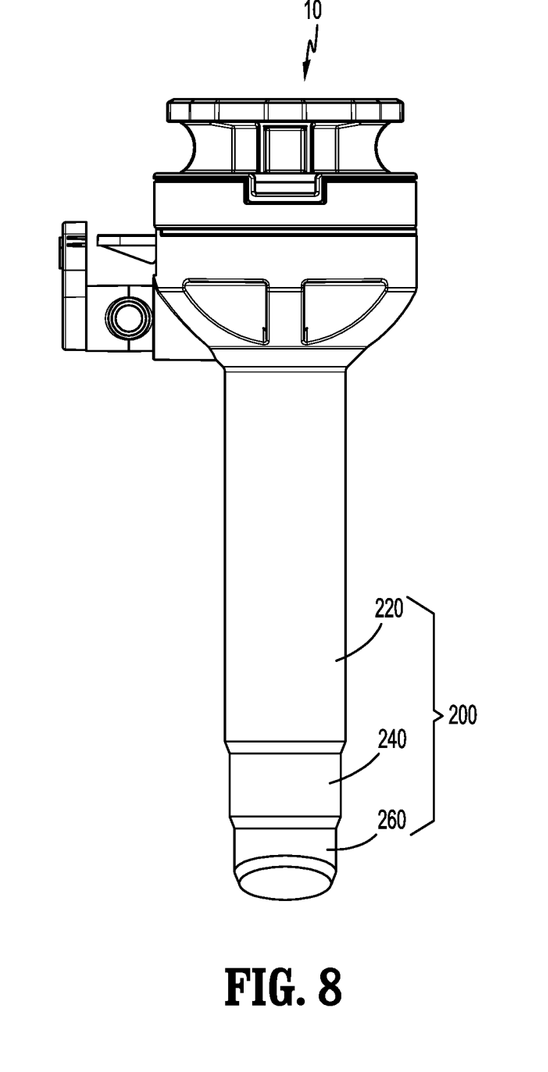
FIG. 8 is a side view of the cannula assembly of FIG. 7.

FIGS. 7 and 8 illustrate the cannula assembly 10 having the first length, in which, the elongate shaft assembly 200 is in the retracted configuration. In particular, the distal end portion 246 of the second segment 240 is adjacent the distal end portion 226 of the first segment 220. The distal end portion 266 of the third segment 260 is adjacent the distal end portion 246 of the second segment 240.

Figure 9:
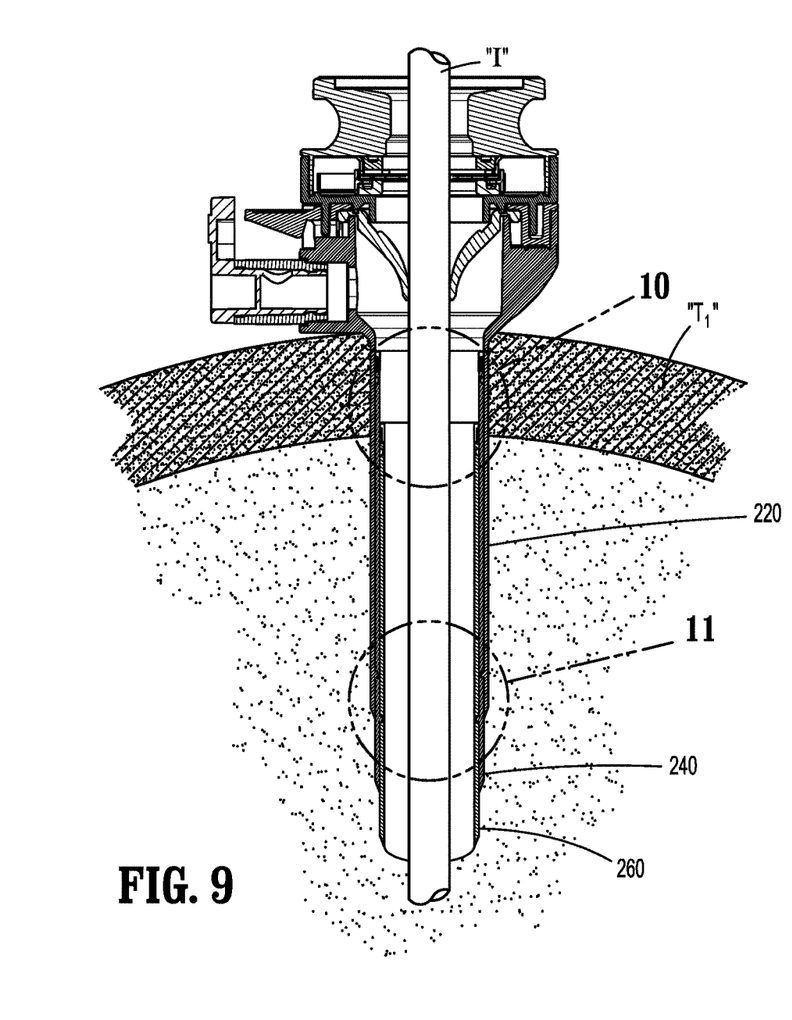
FIG. 9 is a side cross-sectional view of the cannula assembly of FIG. 7 taken along section line 9-9 of FIG. 7, illustrating use with a surgical instrument inserted therethrough and into a surgical site.
Figure 10:
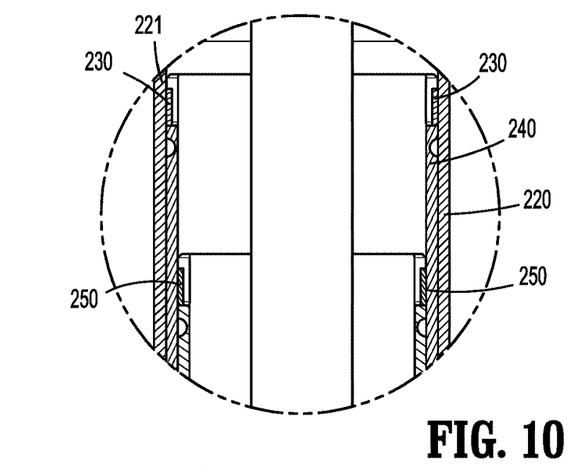
FIG. 10 is an enlarged cross-sectional view of the indicated area of detail of FIG. 9.
Figure 11:
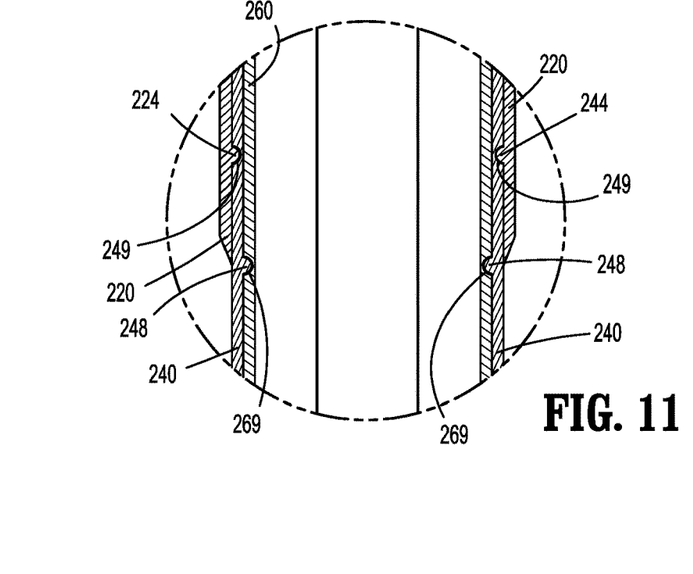
FIG. 11 is an enlarged cross-sectional view of the indicated area of detail of FIG. 9.

FIGS. 9-11 illustrate the first, second, and third segments 220, 240, 260 that are nested and in the retracted configuration. The gasket 230 of the second segment 240 engages an inner surface of the proximal end portion 221 of the first segment 220 in a sealing relation to inhibit loss of, e.g., the insufflation fluid. The gasket 250 of the third segment 260 engages an inner surface of the proximal end portion 242 (FIG. 3) of the second segment 240 in a sealing relation to inhibit loss of, e.g., the insufflation fluid. When the elongate shaft assembly 200 is in the retracted configuration, the first circular protrusion 224 of the first segment 220 is received in the distal circular groove 249 of the second segment 240 to inhibit axial displacement of the second segment 240 relative to the first segment 220 during use. Further, the second circular protrusion 248 of the second segment 240 is received in the distal circular groove 269 of the third segment 260 to inhibit axial displacement of the second segment 240 relative to the third segment 260 during use. Further, the gaskets 230, 250 may be formed of materials to provide, e.g., a fluid-tight, seal and frictional securement against the respective inner surfaces of the first and second segments 220, 240.

Figure 12:
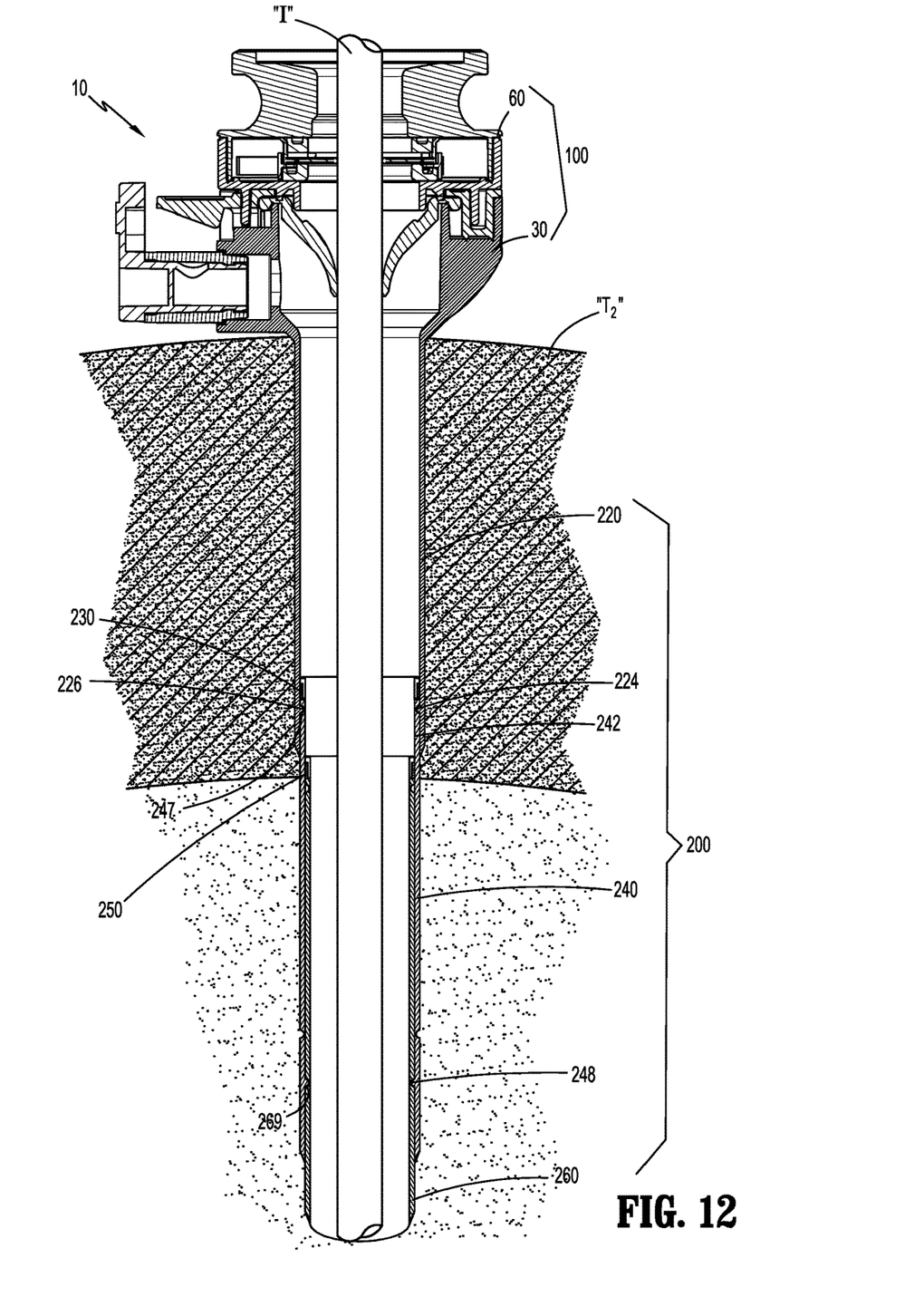
FIG. 12 is a cross-sectional view of the cannula assembly of FIG. 1 taken along section line 12-12 of FIG. 1, illustrating the cannula assembly in an intermediate configuration and inserted into a surgical site.

FIG. 12 illustrates the elongate shaft assembly 200 in the intermediate configuration such that the cannula assembly 10 has a second length greater than the first length. In the intermediate configuration, the gasket 230 of the second segment 240 engages the inner surface of the distal end portion 226 of the first segment 220. Further, the first circular protrusion 224 of the first segment 220 is received in the proximal circular groove 247 of the second segment 240 to inhibit axial displacement of the second segment 240 relative to the first segment 220 during use. In addition, the gasket 250 of the third segment 260 engages the inner surface of the proximal end portion 242 of the second segment 240 in a sealing relation. The second circular protrusion 248 of the second segment 240 is received in the distal circular groove 269 of the third segment 260 to inhibit axial displacement of the third segment 260 relative to the second segment 240 during use.

Figure 13:
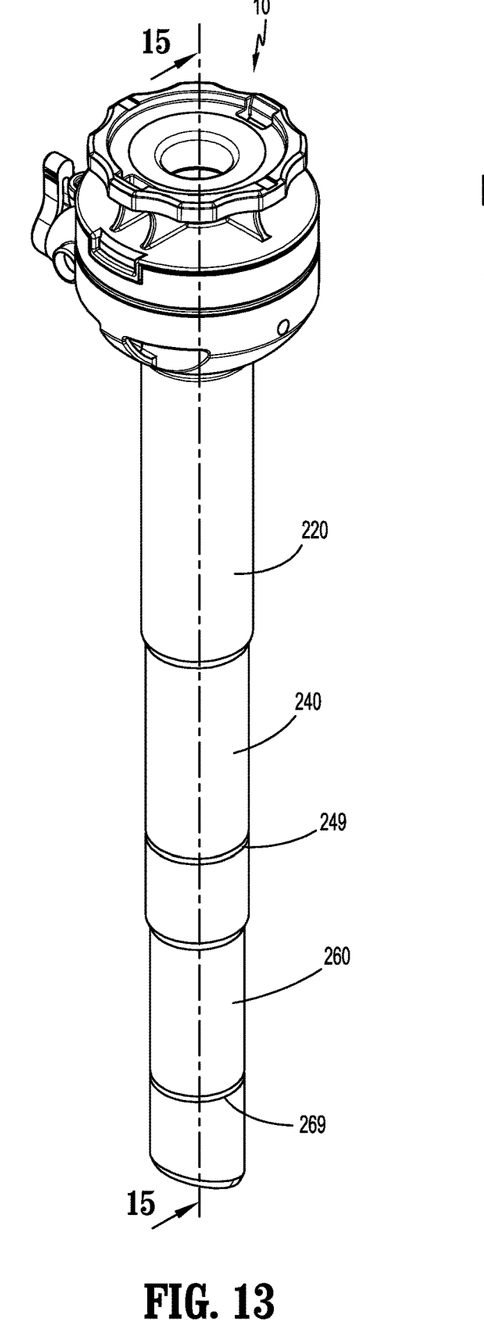
FIG. 13 is a perspective view of the cannula assembly of FIG. 1 in an extended configuration.
Figure 14:
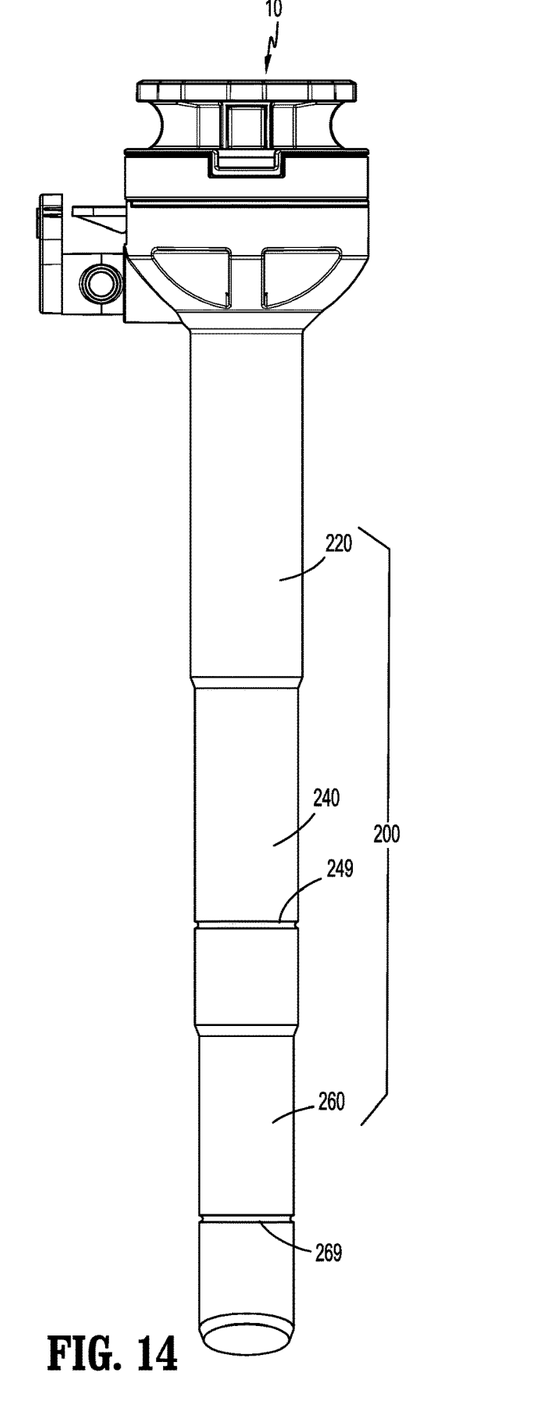
FIG. 14 is a side view of the cannula assembly of FIG. 13.
Figure 15:
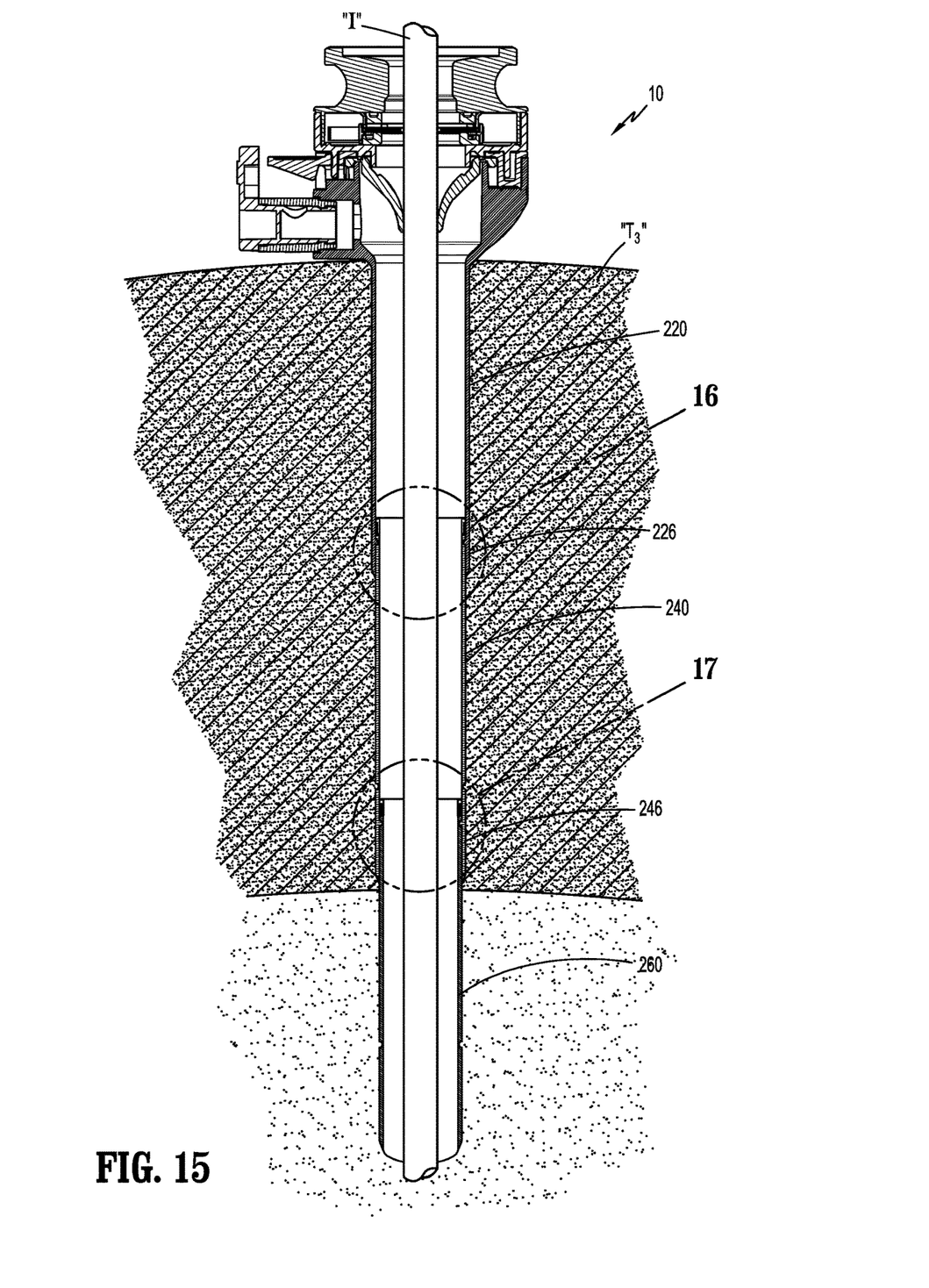
FIG. 15 is a cross-sectional view of the cannula assembly of FIG. 13 taken along section line 15-15, illustrating use with a surgical instrument extending through the cannula assembly and into a surgical site.
Figure 16:
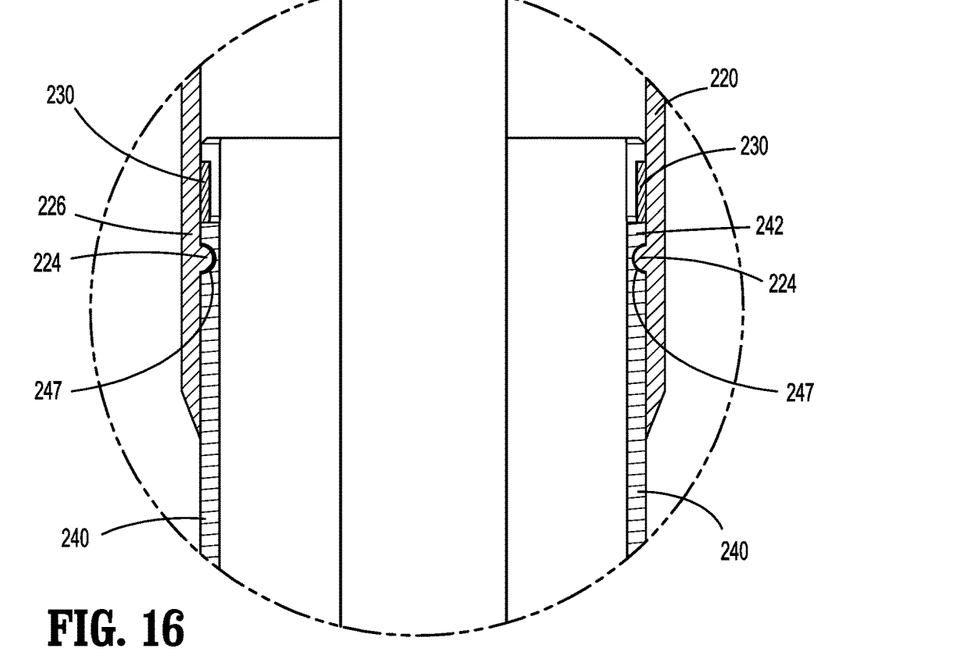
FIG. 16 is an enlarged cross-sectional view of the indicated area of detail of FIG. 15.
Figure 17:
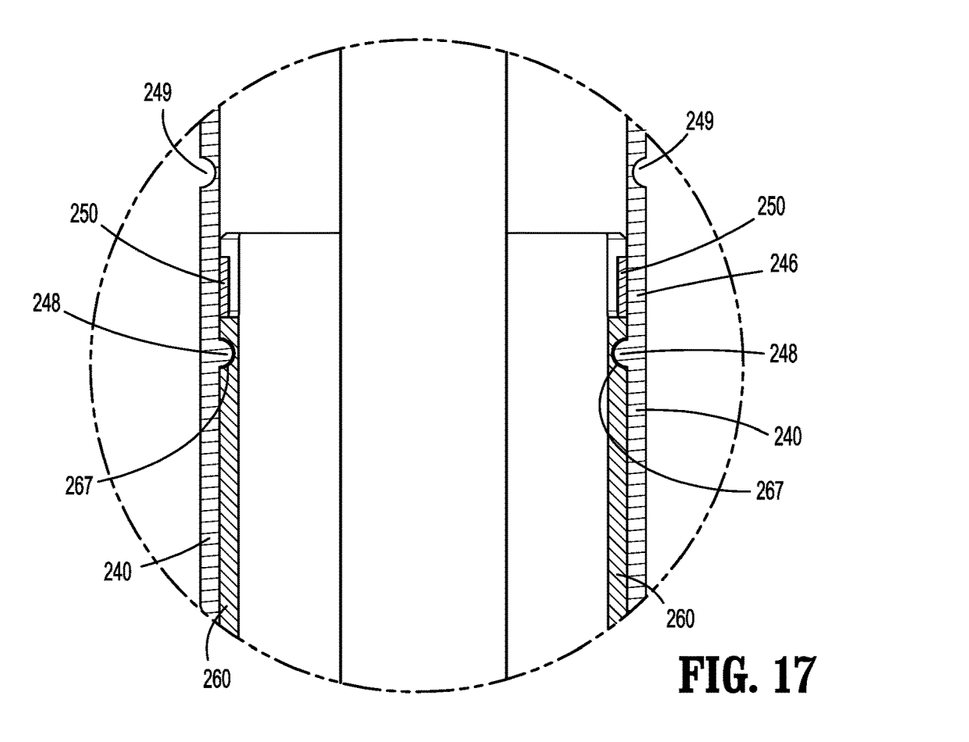
FIG. 17 is an enlarged cross-sectional view of the indicated area of detail of FIG. 15.

FIGS. 13 and 14 illustrate the elongate shaft assembly 200 in the extended configuration, in which, the cannula assembly 10 has a third length greater than the second length. FIGS. 15-17 illustrate the second segment 240 secured to the distal end portion 226 of the first segment 220, and the third segment 260 secured to the distal end portion 246 of the second segment 240. In particular, the gasket 230 of the second segment 240 engages the inner surface of the distal end portion 226 of the first segment 220 in a sealing relation. Further, the first circular protrusion 224 of the first segment 220 is received in the proximal circular groove 247 of the proximal end portion 242 of the second segment 240 to inhibit axial displacement of the second segment 240 relative to the first segment 220. In addition, the gasket 250 of the third segment 260 engages the inner wall of the distal end portion 246 of the second segment 240 in a sealing relation. Further, the second circular protrusion 248 of the second segment 240 is received in the proximal circular groove 267 of the third segment 260 to inhibit axial displacement of the third segment 260 relative to the second segment 240 during use. Under such a configuration, the clinician may selectively adjust the length of the cannula assembly 10 by transitioning the elongate shaft assembly 200 to any one of the three configurations. For example, the cannula assembly 10 may be adjusted to be in the retracted configuration when utilized for use with tissue "$T_1$" having a small thickness (FIG. 9), and in the extended configuration when utilized for use with tissue "$T_3$" having a large thickness (FIG. 15). The cannula assembly 10 may be adjusted to be in the intermediate configuration when utilized for use with tissue "$T_2$" having a medium thickness (FIG. 12). In this manner, a single cannula assembly 10 may be adjusted to be suitable for a particular patient, thereby reducing the need for various cannula assemblies 10. It is contemplated that the first, second, and third segments 220, 240, 260 may be positioned to provide other lengths of the cannula assembly 10. For example, the second segment 240 may be positioned between the proximal and distal end portions 221, 226 of the first segment 220.

Initially, the elongate shaft assembly 200 is adjusted by the clinician to provide a desired length of the cannula assembly 100. For example, the length of the cannula assembly 10 may be tailored to the patient or the surgical procedure being performed. An incision is made in a body wall to gain entry to a body cavity, such as the abdominal cavity. The distal end portion 266 of the third segment 260 of the elongate shaft assembly 200 is inserted through the incision until at least the distal end portion 266 of the third segment 260 is within the body cavity. The base portion 30 of the cannula housing 100 may rest on the patient such that the base portion 30 and the elongate shaft assembly 200 engage tissue in a sealing relation. With the incision sealed, the body cavity may be insufflated with $CO_2$, a similar gas, or another insufflation fluid. Surgical instruments may be inserted through the cannula assembly 10 to perform desired surgical procedures.

It is further contemplated that the cannula assembly 10 may be used with an obturator. The obturator generally includes a head portion having latches configured to engage respective notches defined in the cannula housing 100 of the cannula assembly 10 to enhance securement therewith, an elongate shaft extending from the head portion, and an optical penetrating tip coupled to a distal end of the elongate shaft. The optical penetrating tip may be used to penetrate the skin and access the body cavity. By applying pressure against the proximal end of the obturator, the tip of the obturator is forced though the skin and the underlying tissue layers until the cannula and obturator enter the body cavity.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A cannula assembly comprising:
    a cannula housing; and
    an elongate shaft assembly extending from the cannula housing, the elongate shaft assembly defining a lumen in communication with the cannula housing, the elongate shaft assembly including:
        a first segment coupled to the cannula housing;
        a second segment slidable relative to the first segment;
        an engaging portion disposed in a proximal portion of the second segment, the engaging portion defining a circular recess and having slots, the slots configured to enable the engaging portion to flex radially with respect to a longitudinal axis of the second segment and facilitate slidable movement of the second segment relative to the first segment;
        a gasket disposed in the circular recess and configured to engage an inner surface of the first segment in a sealing relation; and
        a third segment slidable relative to the second segment, wherein the elongate shaft assembly is transitionable to a retracted configuration, in which the cannula assembly has a first length, an intermediate configuration, in which the cannula assembly has a second length greater than the first length, and an extended configuration, in which the cannula assembly has a third length greater than the second length.

2. The cannula assembly according to claim 1, wherein the first segment includes a first circular protrusion extending radially inward from an inner surface of the first segment.

3. The cannula assembly according to claim 2, wherein the first circular protrusion is disposed in a distal end portion of the first segment.

4. The cannula assembly according to claim 2, wherein the second segment includes a proximal circular groove configured to receive the first circular protrusion of the first segment.

5. The cannula assembly according to claim 2, wherein the second segment includes a distal circular groove configured to receive the first circular protrusion of the first segment.

6. The cannula assembly according to claim 2, wherein the second segment includes a second circular protrusion extending radially inward from an inner surface of the second segment.

7. The cannula assembly according to claim 6, wherein the second circular protrusion of the second segment is disposed adjacent a distal end portion of the second segment.

8. The cannula assembly according to claim 7, wherein the third segment includes proximal and distal circular grooves configured to receive the second circular protrusion of the second segment.

9. The cannula assembly according to claim 1, wherein the cannula housing includes a base portion coupled to the first segment extending from the base portion and a seal assembly detachably coupled to the base portion.

10. The cannula assembly according to claim 1, wherein the engaging portion includes fingers extending along the longitudinal axis of the second segment and adjacent fingers are separated by one of the slots.

11. The cannula assembly according to claim 10, wherein the fingers flex radially with respect to the longitudinal axis of the second segment.

12. A cannula assembly comprising:
    a cannula housing configured to receive a surgical instrument; and
    an elongate shaft assembly coupled to the cannula housing, the elongate shaft assembly adjustable to selectively vary a length of the cannula assembly, the elongate shaft assembly defining a lumen configured to receive the surgical instrument inserted through the cannula housing, the elongate shaft assembly including:
        a first segment coupled to the housing;
        a second segment slidably extending from the first segment;
        an engaging portion disposed in a proximal portion of the second segment, the engaging portion defining a circular recess and having slots, the slots configured to enable the engaging portion to flex radially with respect to a longitudinal axis of the second segment and facilitate slidable movement of the second segment relative to the first segment;
        a gasket disposed in the circular recess and configured to engage an inner surface of the first segment in a sealing relation; and
        a third segment slidably extending from the second segment,
    wherein the elongate shaft assembly is transitionable to:
    a retracted configuration, in which a proximal portion of the second segment is disposed adjacent a proximal portion of the first segment and a proximal portion of the third segment is disposed adjacent the proximal portion of the second segment;
    an intermediate configuration, in which the proximal portion of the second segment is disposed adjacent a distal portion of the first segment and the proximal portion of the third segment is adjacent the proximal portion of the second segment; and
    an extended configuration, in which the proximal portion of the second segment is disposed adjacent the distal portion of the first segment and the proximal portion of the third segment is disposed adjacent a distal portion of the second segment.

13. The cannula assembly according to claim 12, wherein the first, second, and third segments are concentrically arranged.

14. The cannula assembly according to claim 12, wherein the second segment engages an inner surface of the first segment in a sealing relation.

15. The cannula assembly according to claim 12, wherein the third segment engages an inner surface of the second segment in a sealing relation.

16. The cannula assembly according to claim 12, wherein the first segment includes a mating portion at the distal portion of the first segment.

17. The cannula assembly according to claim 16, wherein the second segment includes proximal and distal mating portions complementary to the mating portion of the first segment to inhibit axial displacement of the second segment relative to the first segment.

18. The cannula assembly according to claim 17, wherein the second segment includes a mating part and the third segment includes proximal and distal mating parts complementary to the mating part of the second segment to inhibit axial displacement of the third segment relative to the second segment.

19. The cannula assembly according to claim 12, wherein the engaging portion includes fingers extending along the longitudinal axis of the second segment and adjacent fingers are separated by one of the slots.

20. The cannula assembly according to claim 19, wherein the fingers flex radially with respect to the longitudinal axis of the second segment.

* * * * *